United States Patent
O'Loughlin et al.

(10) Patent No.: US 6,587,729 B2
(45) Date of Patent: Jul. 1, 2003

(54) APPARATUS FOR AUDIBLY COMMUNICATING SPEECH USING THE RADIO FREQUENCY HEARING EFFECT

(75) Inventors: James P. O'Loughlin, Placitas, NM (US); Diana L. Loree, Albuquerque, NM (US)

(73) Assignee: The United States of America as represented by the Secretary of the Air Force, Washington, DC (US)

( * ) Notice: Subject to any disclaimer, the term of this patent is extended or adjusted under 35 U.S.C. 154(b) by 0 days.

(21) Appl. No.: 10/131,626

(22) Filed: Apr. 24, 2002

(65) Prior Publication Data

US 2002/0123775 A1 Sep. 5, 2002

Related U.S. Application Data

(62) Division of application No. 08/766,687, filed on Dec. 13, 1996, now Pat. No. 6,470,214.

(51) Int. Cl.$^7$ ................................................ H03C 1/54
(52) U.S. Cl. ........................ 607/55; 128/897; 332/167; 381/151; 600/586
(58) Field of Search .......................... 332/167; 381/151; 607/56, 55; 340/384.1; 600/559, 23, 586; 128/897, 898

(56) References Cited

U.S. PATENT DOCUMENTS

| | | | | |
|---|---|---|---|---|
| 3,563,246 A | * | 2/1971 | Puharich et al. .............. 607/55 |
| 3,629,521 A | * | 12/1971 | Puharich et al. .............. 607/56 |
| 4,835,791 A | * | 5/1989 | Daoud ........................ 375/301 |
| 5,450,044 A | * | 9/1995 | Hulick ........................ 332/103 |

* cited by examiner

*Primary Examiner*—Kennedy Schaetzle
(74) *Attorney, Agent, or Firm*—James M. Skorich

(57) ABSTRACT

A modulation process with a fully suppressed carrier and input preprocessor filtering to produce an encoded output; for amplitude modulation (AM) and audio speech preprocessor filtering, intelligible subjective sound is produced when the encoded signal is demodulated using the RF Hearing Effect. Suitable forms of carrier suppressed modulation include single sideband (SSB) and carrier suppressed amplitude modulation (CSAM), with both sidebands present.

11 Claims, 3 Drawing Sheets

APPARATUS FOR AUDIBLY COMMUNICATING SPEECH USING THE RADIO FREQUENCY HEARING EFFECT

This application is a division of U.S. patent application Ser. No. 08/766,687 filed on Dec. 13, 1996, now U.S. Pat. No. 6,470,214, and claims the benefit of the foregoing filing date.

The invention described herein may be manufactured and used by or for the Government for governmental purposes without the payment of any royalty thereon.

BACKGROUND OF THE INVENTION

This invention relates to the modulating of signals on carriers, which are transmitted and the signals intelligibly recovered, and more particularly, to the modulation of speech on a carrier and the intelligible recover of the speech by means of the Radio Frequency Hearing Effect.

The Radio Frequency ("RF") Hearing Effect was first noticed during World War II as a subjective "click" produced by a pulsed radar signal when the transmitted power is above a "threshold" level. Below the threshold level, the click cannot be heard.

The discovery of the Radio Frequency Hearing Effect suggested that a pulsed RF carrier could be encoded with an amplitude modulated ("AM") envelope. In one approach to pulsed carrier modulation, it was assumed that the "click" of the pulsed carrier was similar to a data sample and could be used to synthesize both simple and complex tones such as speech. Although pulsed carrier modulation can induce a subjective sensation for simple tones, it severely distorts the complex waveforms of speech, as has been confirmed experimentally.

The presence of this kind of distortion has prevented the click process for the encoding of intelligible speech. An example is provided by AM sampled data modulation Upon demodulation the perceived speech signal has some of the envelope characteristics of an audio signal. Consequently a message can be recognized as speech when a listener is pre-advised that speech has been sent. However, if the listener does not know the content of the message, the audio signal is unintelligible.

The attempt to use the click process to encode speech has been based on the assumption that if simple tones can be encoded, speech can be encoded as well, but this is not so. A simple tone can contain several distortions and still be perceived as a tone whereas the same degree of distortion applied to speech renders it unintelligible.

SUMMARY OF THE INVENTION

In accomplishing the foregoing and related object the invention uses a modulation process with a fully suppressed carrier and pre-processor filtering of the input to produce an encoded output. Where amplitude modulation (AM) is employed and the pre-processor filtering is of audio speech input, intelligible subjective sound is produced when the encoded signal is demodulated by means of the RF Hearing Effect. Suitable forms of carrier suppressed modulation include single sideband (SSB) and carrier suppressed amplitude modulation (CSAM), with both sidebands present.

The invention further provides for analysis of the RE hearing phenomena based on an RF to acoustic transducer model. Analysis of the model suggests a new modulation process which permits the RF Hearing Effect to be used following the transmission of encoded speech.

In accordance with one aspect of the invention the pre-processing of an input speech signal takes place with a filter that de-emphasizes the high frequency content of the input speech signal. The de-emphasis can provide a signal reduction of about 40 dB (decibels) per decade. Further processing of the speech signal then takes place by adding a bias level and taking a root of the predistorted waveform. The resultant signal is used to modulated an RF carrier in the AM fully suppressed carrier mode, with single or double sidebands.

The modulated RF signal is demodulated by an RF to acoustic demodulator that produces an intelligible acoustic replication of the original input speech.

The RF Hearing Effect is explained and analyzed as a thermal to acoustic demodulating process. Energy absorption in a medium, such as the head, causes mechanical expansion and contraction, and thus an acoustic signal.

When the expansion and contraction take place in the head of an animal, the acoustic signal is passed by conduction to the inner ear where it is further processed as if it were an acoustic signal from the outer ear.

The RF to Acoustic Demodulator thus has characteristics which permit the conversion of the RF energy input to an acoustic output.

Accordingly, it is an object of the invention to provide a novel technique for the intelligible encoding of signals. A related object is to provide for the intelligible encoding of speech.

Another object of the invention is to make use of the Radio Frequency ("RF") Hearing Effect in the intelligible demodulation of encoded signals, including speech.

Still another object of the invention is to suitably encode a pulsed RF carrier with an amplitude modulated ("AM") envelope such that the modulation will be intelligibly demodulated by means of the RF Hearing Effect. A related object is to permit a message to be identified and understood as speech when a listener does not know beforehand that the message is speech.

Other aspects of the invention will be come apparent after considering several illustrative embodiments, taken in conjunction with the drawings.

DETAINED DESCRIPTION OF THE PREFERRED EMBODIMENT

Figure 1:
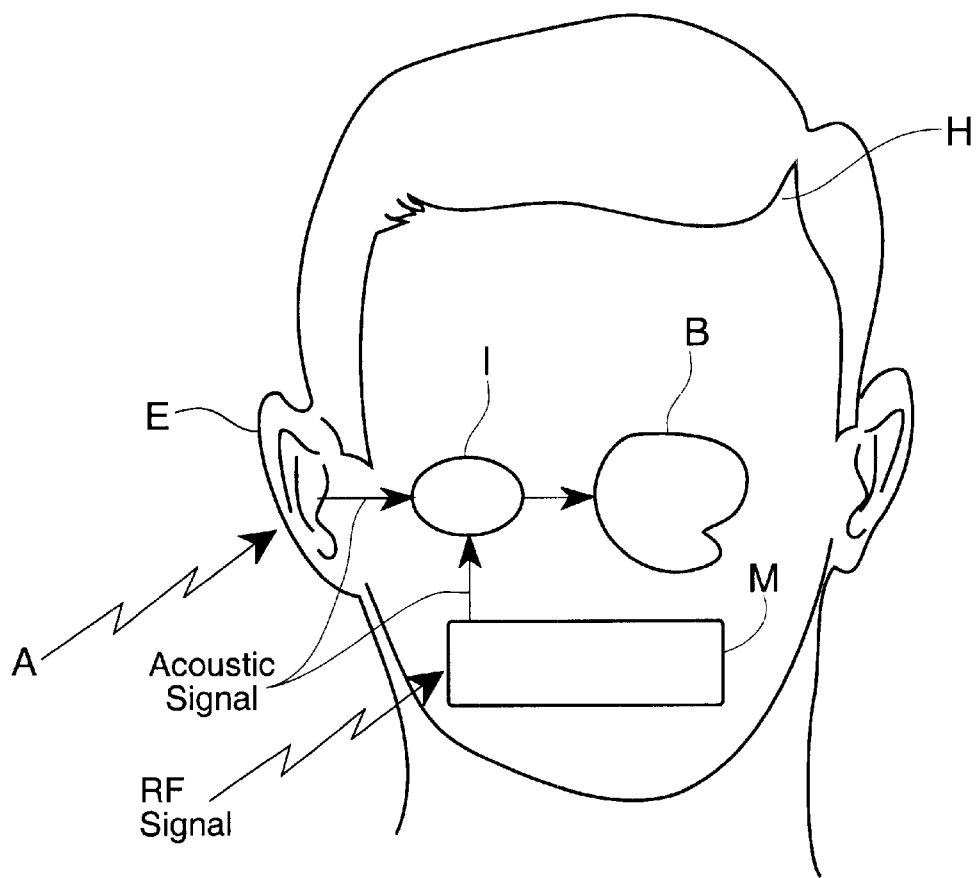
FIG. 1 is a block diagram model of RF to Acoustic Demodulation Process making use of the Radio Frequency ("RF") Hearing Effect.
Figure 2:
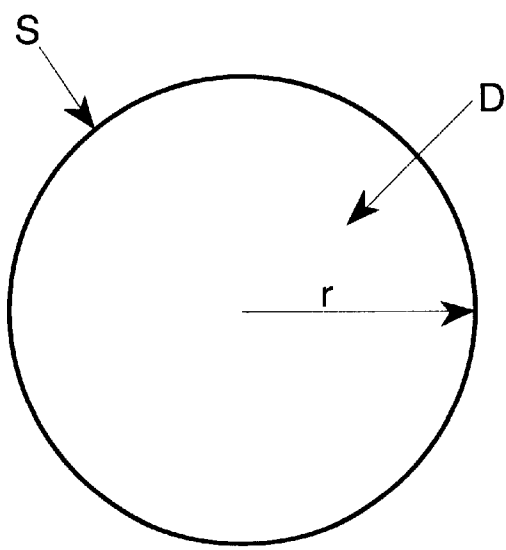
FIG. 2 is a spherical demodulator and radiator having a specific acoustic impedance for demodulation using the RF Hearing Effect.

With reference to the drawings, FIG. 1 illustrates the RF to acoustic demodulation process of the invention. Ordinarily an acoustic signal A reaches the outer ear E of the head H and traverses first to the inner ear I and then to the acoustic receptors of the brain B. A modulated RF signal, however, enters a demodulator D, which is illustratively provided by the mass M of the brain, and is approximated, as shown in FIG. 2, by a sphere S of radius r in the head H. The radius r of the sphere S is about 7 cm to make the sphere S equivalent to about the volume of the brain B. It will be appreciated that where the demodulator D, which can be an external component, is not employed with the acoustic receptors of the brain B, it can have other forms.

The sphere S, or its equivalent ellipsoid or similar solid, absorbs RF power which causes an increase in temperature that in turn causes an expansion and contraction which results in an acoustic wave. As a first approximation, it is assumed that the RF power is absorbed uniformly in the brain. Where the demodulator D is external to the brain B, the medium and/or RF carrier frequency can be selected to assure sufficiently uniform absorption.

For the modulated RF signal of FIG. 1, the power absorbed in the sphere S is proportional to the power waveform of the modulated RF signal. The absorption rate is characterized quantitatively in terms of the SAR (Specific Absorption Rate) in the units of absorbed watts per kilogram per incident watt per square centimeter.

The temperature of the sphere S is taken as following the integrated heat input from the power waveform, i.e. the process is approximated as being adiabatic, at least for short term intervals on the order of a few minutes.

The radial expansion of the sphere follows temperature and is converted to sound pressure, p(t), determined by the radial velocity ($U_r$) multiplied by the real part of the specific acoustic impedance ($Z_s$) of the sphere, as indicated in equation (1), below.

$$Z_s = \rho_o c(jkr)/(1+jkr) = \rho_o c \, jf/f_c/(1+jf/f_c) \quad (1)$$

Where:

$\rho_o$=density, 1000 kg/m$^3$ for water c=speed of sound, 1560 m/s, in water @ 37° C.

k=wave number, $2\pi$/wavelength r=sphere radius, in meters (m)

f=audio frequency $f_c$=lower cutoff break frequency,=$c/(2\pi r)$ j=the 90 degree phase-shift operator The specific acoustic impedance for a sphere of 7 cm radius, on the order of the size of the brain, has a lower cut-off break frequency of about 3,547 Hertz (Hz) for the parameters given for equation (1). The essential frequency range of speech is about 300 to 3000 Hz, i.e., below the cut-off frequency. It is therefore the Real part ($R_e$) of $Z_s$ times the radial particle velocity ($U_r$) which determines the sound pressure, p(t). The real part of $Z_s$ is given by equation (1a), below:

$$R_e(Z_s) = \rho_o c(f/f_c)^2/(1+(f/f_c)^2) \quad (1a)$$

In the speech spectrum, which is below the brain cut-off frequency, the sphere S is an acoustic filter which "rolls off", i.e. decreases in amplitude at −40 dB per decade with decreasing frequency. In addition to any other demodulation processes to be analyzed below, the filter characteristics of the sphere will modify the acoustic signal with a 40 dB per decade slope in favor of the high frequencies.

Results for an AM Modulated Single Tone

An RF carrier with amplitude $A_c$ at frequency $\omega_c$ is AM modulated 100 percent with a single tone audio signal at frequency $\omega_1$. The voltage (time) equation of this modulated signal is given by equation (2), below:

$$V(t) = A_c \sin(\omega_c t)(1+\sin(\omega_a t)) \quad (2)$$

The power signal is $V(t)^2$ as given by equation (3), below:

$$P(t) = A_c^2[\tfrac{3}{4} + \sin(\omega_3 t) - \tfrac{1}{4}\cos(2\omega_3 t) - \tfrac{3}{4}\cos(2\omega_c t) - \cos(2\omega_c t)$$
$$\sin(\omega_3 t) + \tfrac{1}{4}\cos(2\omega_c t)\cos(2\omega_3 t)] \quad (3)$$

To find the energy absorbed in the sphere, the time integral of equation (3) is taken times absorption coefficient, K. The result is divided by the specific heat, SH to obtain the temperature of the sphere and then multiplied by the volume expansion coefficient, Mv to obtain the change in volume. The change in volume is related to the change in radius by equation (4), below:

$$dV/V = 3dr/r \quad (4)$$

To obtain the amplitude of the radius change, there is multiplication by the radius and division by three. The rms radial surface velocity, $U_r$ is determined by multiplying the time derivative by r and dividing by $2^{1/2}$. The result, $U_r$, is proportional to the power function, P(t) in equation (5), below.

$$U_r = 0.3535 \, P(t) r K M_v/(3SH) \quad (5)$$

The acoustic pressure, p(t), is given in equation (6), below, as the result of multiplying equation (5) by the Real part of the specific acoustic impedance, $R_e$ (1).

$$p(t) = R_e\{Z_s U_r\} = R_e(Z_s) U_r \quad (6)$$

The SPL (Sound Pressure Level), in acoustic dB, is approximated as 20 log[p(t)/2E−5]. The standard acoustic reference level of 2E−5 Newtons per square meter is based on a signal in air; however, the head has a water-like consistency. Therefore, the subjective level in acoustic dB is only approximate, but sufficient for first order accuracy.

In a single tone case the incident RF power, P(t), from equation (3) has two terms as shown in equation (7), below, which are in the hearing range.

$$\sin(\omega_a t) - \tfrac{1}{4}\cos(2\omega_a t) \quad (7)$$

This is converted to the acoustic pressure wave, p(t), by multiplying by the specific acoustic impedance calculated at the two frequencies. Therefore, the resulting pressure wave as indicated in equation (8), below, becomes $$p(t) = C[Z_s(\omega_a)\sin(\omega_a t) - \tfrac{1}{4} Z_s(2\omega_a)\cos(2\omega_3 t)] \quad (8)$$

The result is an audio frequency and a second harmonic at about ¼ amplitude. Thus using an RF carrier, AM modulated by a single tone, the pressure wave audio signal will consist of the audio tone and a second harmonic at about −6 dB, if the specific acoustic impedances at the two frequencies are the same. However, from equation (1) the break frequency of a model 7 cm sphere is 3.547 Hz. Most of the speech spectrum is below this frequency therefore the specific acoustic impedance is reactive and the real component is given by equation (8a), below:

$$R_e\{Z_s(f)\} = \rho_o c(f/f_c)^2/(1+(f/f_c)) \quad (8a)$$

Below the cutoff frequency the real part of the impedance varies as the square of the frequency or gives a boost of 40 dB per decade. Therefore, if the input modulation signal is 1 kHz, the second harmonic will have a boost of about 4 time in amplitude, or 12 dB, due to the variation of the real part of the specific acoustic impedance with frequency. So the second harmonic pressure term in equation (8) is actually four times the power or 6 dB higher than the fundamental term. If the second harmonic falls above the cutoff frequency then the boost begins to fall back to 0 dB. However, for most of the speech spectrum there is a sever distortion and strong boost of the high frequency distortion components.

Results for Two Tone AM Modulation Analysis

Because of the distortion attending single tone modulation, predistortion of the modulation could be attempted such that the resulting demodulated pressure wave will not contain harmonic distortion. This will not work, however, because of the non-linear cross-products of two-tone modulation are quite different from single tone modulation as shown below.

Nevertheless, two-tone modulation distortion provides an insight for the design of a corrective process for a complex modulation signal such as speech. The nature of the distortion is defined in terms of relative amplitudes and frequencies.

Equation (8b) is that of an AM modulated carrier for the two-tone case where $\omega_{a1}$ and $\omega_{a2}$ are of equal amplitude and together modulate the carrier to a maximum peak value of 100 percent. The total modulated RF signal is given by equation (8b), below:

$$V(t)=A_c \sin(\omega_c t)[1+\frac{1}{2} \sin(\omega_{a1}t)+\frac{1}{2} \sin(\omega_{a2}t)]$$

The square of (8b) is the power signal, which has the same form as the particle velocity, $U_r(t)$, of equation (9), below.

From the square of (8b) the following frequencies and relative amplitudes are obtained for the particle velocity wave, $U_r(t)$, which are in the audio range;

$$U_r(t)=C[\sin(\omega_{a1}t)+\sin(\omega_{a2}t)+\frac{1}{4}\cos((\omega_{a1}-\omega_{a2})(t)=\frac{1}{4}\cos((\omega_{a1}+\omega_{a2})t)-\frac{1}{8}\cos(2\omega_{a1}t)-\frac{1}{8}\cos(2\omega_{a2}t)] \quad (9)$$

If the frequencies in equation (9) are below the cut-off frequency, the impedance boost correction will result in a pressure wave with relative amplitudes given in equation (9a), below:

$$p(t)=C'[\sin(\omega_{a1}t)+b^2 \sin(\omega_{a2}t)+(1-b^2)/4 \cos((\omega_{a1}-\omega_{a2})t)+(1+b^2)/4 \cos((\omega_{a1}+\omega_{a2})t)-\frac{1}{2}\cos(2\omega_{a1}t)-b^2/2 \cos(2\omega_{a2}t) \quad (9a)$$

where: $b=\omega_{a2}/\omega_{a1}$ and $\omega_{a2}>\omega_{a1}$

Equation (9a) contains a correction factor, b, for the specific acoustic impedance variation with frequency. The first two terms of (9a) are the two tones of the input modulation with the relative amplitudes modified by the impedance correction factor. The other terms are the distortion cross products which are quite different from the single tone distortion case. In addition to the second harmonics, there are sum and difference frequencies. From this two-tone analysis it is obvious that more complex multiple tone modulations, such as speech, will be severely distorted with even more complicated cross-product and sum and difference components. This is not unexpected since the process which creates the distortion is nonlinear. This leads to the conclusion that a simple passive predistortion filter will not work on a speech signal modulated on an RF carrier by a conventional AM process, because the distortion is a function of the signal by a nonlinear process.

However, the serious distortion problem can be overcome by means of the invention which exploits the characteristics of a different type of RF modulation process in addition to special signal processing.

AM Modulation With Fully Suppressed Carrier for the Intelligible Encoding of Speech by the Invention for Compatibility With the RF Hearing Phenomena The equation for AM modulation with a fully suppressed carrier is given by equation (10), below:

$$V(t)=a(t)\sin(\omega_c t) \quad (10)$$

This modulation is commonly accomplished in hardware by means of a circuit known as a balanced modulator, as disclosed, for example in "Radio Engineering", Frederick E. Terman, p.481–3, McGraw-Hill, 1947.

The power signal has the same form as the particle velocity signal which is obtained from the square of equation (10) as shown in equation (11), below:

$$P(t)=C\ U_r=a(t)^2/2-(a(t)^2/2)\cos(2\omega_c t)) \quad (11)$$

From inspection of equations (10) and (11) it is seen that, if the input audio signal, a(t), is pre-processed by taking the square root and then modulating the carrier, the audio term in the particle velocity equation will be an exact, undistorted, replication of the input audio signal. Since the audio signal from a microphone is bipolar, it must be modified by adding a very low frequency (essential d.c.) bias term, A, such that the resultant sum, [a(t)+A]>0.0, is always positive. This is necessary in order to insure a real square root. The use of a custom digital speech processor implements the addition of the term A, i.e. as shown in equation (10*), below:

$$V(t)=(a(t)+A)^{1/2} \sin(\omega_c t) \quad (10^*)$$

The pressure wave is given by equation (11*), below:

$$p(t)=C\ U_r=A/2+a(t)/2-(a(t)/2)\cos(2\omega_c t)-(A/2)\cos(2\omega_c t) \quad (11^*)$$

When the second term of the pressure wave of equation (11*) is processed through the specific acoustic impedance it will result in the replication of the input audio signal but will be modified by the filter characteristics of the Real part of the specific acoustic impedance, $R_e\{Z_s(f)\}$, as given in equation (8a). The first term of equation (11*) is the d.c. bias, which is added to obtain a real square root; it will not be audible or cause distortion. The third and fourth terms of (11*) are a.c. terms at twice the carrier frequency and therefore will not distort or interfere with the audio range signal, a(t).

Since the filter characteristic of equation (7) is a linear process in amplitude, the audio input can be predistorted before the modulation is applied to the carrier and then the pressure or wound wave audio signal, which is the result of the velocity wave times the impedance function, $R_e\{Z_s(f)\}$, will be the true replication of the original input audio signal.

Figure 3:
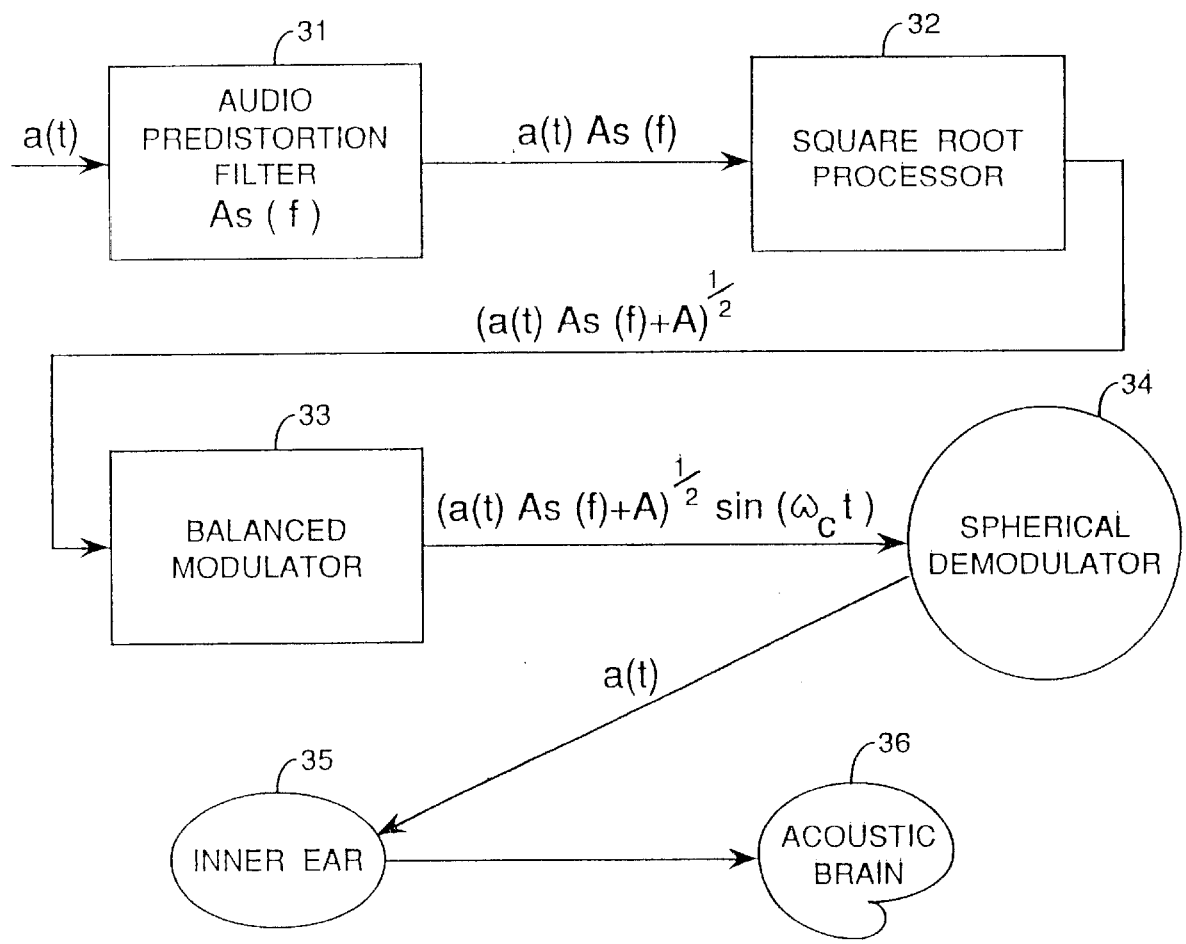
FIG. 3 is a diagram illustrating the overall process and constituents of the invention.

A diagram illustrating the overall system 30 and process of the invention is shown in FIG. 3. Then input signal a(t) is applied to an Audio Predistortion Filter 31 with a filter function As(f) to produce a signal a(t)As(f), which is applied to a Square Root Processor 32, providing an output=(a(t)As(f)+A)$^{1/2}$, which goes to a balanced modulator 33. The modulation process known as suppressed carrier, produces a double sideband output=(a(t)As(f)+A)$^{1/2}$ sin($\omega_c$t), where $\omega_c$ is the carrier frequency. If one of the sidebands and the carrier are suppressed (not shown) the result is single sideband (SSB) modulation and will function in the same manner discussed above for the purposes of implementing the invention. However, the AM double sideband suppressed carrier as described is more easily implemented.

The output of the balanced modulator is applied to a spherical demodulator 34, which recovers the input signal a(t) that is applied to the inner ear 35 and then to the acoustic receptors in the brain 36.

Figure 4:
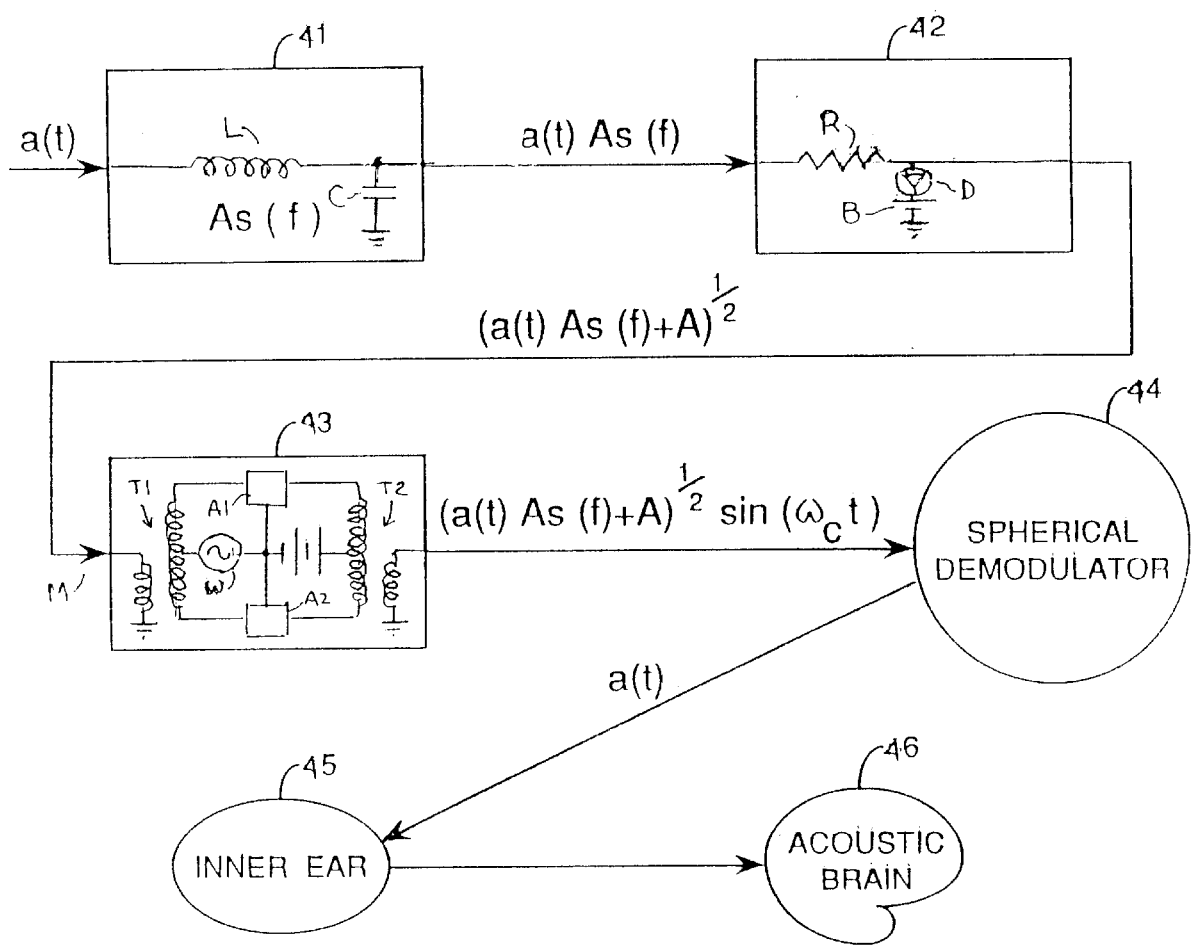
FIG. 4 is an illustrative circuit and wiring diagram for the components of FIG. 3.

The various components 31–33 of FIG. 3 are easily implemented as shown, for example by the corresponding components 41–42 in FIG. 4, where the Filter 41 can take the form of a low pass filter, such as a constant-K filter formed by series inductor L and a shunt capacitor C. Other low-pass filters are shown, for example, in the ITT Federal Handbook, 4th Ed., 1949. As a result the filter output is AS(f) a $1/f^2$. The Root Processor 42 can be implemented by any square-law device, such as the diode D biased by a battery B and in series with a large impedance (resistance) R, so that the voltage developed across the diode D is proportional to the square root of the input voltage a(t)As(f). The balanced modulator 43, as discussed in Terman, op.cit., has symmetrical diodes A1 and A2 with the modulating voltage M applied in opposite phase to the diodes A1 and A2 through an input transformer T1, with the carrier, O, applied commonly to the diodes in the same phase, while the modulating signal is applied to the diodes in opposite phase so that the carrier cancels in the primary of the output transformer T2 and the secondary output is the desired double side band output.

Finally the Spherical Demodulator 45 is the brain as discussed above, or an equivalent mass that provides uniform expansion and contraction due to thermal effects of RF energy.

The invention provides a new and useful encoding for speech on an RF carrier such that the speech will be intelligible to a human subject by means of the RF hearing demodulation phenomena. Features of the invention include the use of AM fully suppressed carrier modulation, the preprocessing of an input speech signal be a compensation filter to de-emphasize the high frequency content by 40 dB per decade and the further processing of the audio signal by adding a bias terms to permit the taking of the square root of the signal before the AM suppressed carrier modulation process.

The invention may also be implemented using the same audio signal processing and Single Sideband (SSB) modulation in place of AM suppressed carrier modulation. The same signal processing may also be used on Conventional AM modulation contains both sideband and the carrier; however, there is a serious disadvantage. The carrier is always present with AM modulation, even when there is no signal. The carrier power does not contain any information but contributes substantially to the heating of the thermal-acoustic demodulator, i.e. the brain, which is undesirable. The degree of this extraneous heating is more than twice the heating caused by the signal or information power in the RF signal. Therefore conventional AM modulation is an inefficient and poor choice compared to the double side-band suppressed carrier and the SSB types of transmissions.

The invention further may be implemented using various degrees of speech compression commonly used with all types of AM modulation. Speech compression is implemented by raising the level of the low amplitude portions of the speech waveform and limiting or compressing the high peak amplitudes of the speech waveform. Speech compression increases the average power content of the waveform and thus loudness. Speech compression introduces some distortion, so that a balance must be made between the increase in distortion and the increase in loudness to obtain the optimum result.

Another implementation is by digital signal processing of the input signal through to the modulation of the RF carrier.

What is claimed is:

1. An apparatus for communicating an audio signal a(t), comprising:

an audio predistortion filter having a filter function As(f) for producing a first output signal a(t)As(t) from the audio signal a(t);

means for adding a bias A to the first output signal, to produce a second output signal a(t)As(f)+A;

a square root processor for producing a third output signal $(a(t)As(f)+A)^{1/2}$ responsive to the second output signal; and a modulator for producing a double sideband output signal responsive to the third output signal, having a carrier frequency of $\omega_c$, and being mathematically described by $(a(t)As(f)+A)^{1/2} \sin(\omega_c t)$; and transmitting the double sideband output signal to a demodulator, whereby the audio signal a(t) is recovered from the double sideband output signal.

2. The communication apparatus defined in claim 1 wherein:

the double sideband output signal has RF power; and the demodulator is for converting the RF power into acoustic pressure waves.

3. The communication apparatus defined in claim 2 wherein:

the demodulator converts the RF power into the acoustic pressure waves by means of thermal expansion and contraction, whereby the acoustic pressure waves approximate the audio signal a(t).

4. The communication apparatus defined in claim 2 wherein the demodulator includes a mass that expands and contracts responsive to the RE power of the double sideband output signal.

5. The communication apparatus defined in claim 4 wherein the mass is approximately spherical.

6. The communication apparatus defined in claim 1 wherein:

the double sideband output signal is comprised of a first sideband component and a second sideband component; and means for suppressing the second sideband component, whereby the demodulator recovers the audio signal a(t) solely from the first sideband component.

7. The communication apparatus defined in claim 1 wherein the audio predistortion filter is a low-pass filter.

8. The communication apparatus defined in claim 7 wherein the audio predistortion filter is a digital processor.

9. The communication apparatus defined in claim 1 wherein:

the square root processor is a diode biased by a voltage source, in series with a resistance, whereby a voltage across the diode is proportional to a square root of the second output signal a(t)As(t)+A.

10. The communication apparatus defined in claim 1 wherein the modulator is a balanced modulator.

11. The communication apparatus defined in claim 1 wherein:

the audio signal a(t) includes a high frequency component; and the audio predistortion filter de-emphasizes the high frequency component by approximately 40 dB per decade.

* * * * *